United States Patent [19]

Furuta et al.

[11] 4,075,100
[45] Feb. 21, 1978

[54] DIALYSIS UNIT AND DIALYSIS APPARATUS EMPLOYING THE DIALYSIS UNIT

[75] Inventors: Tadaaki Furuta; Kenji Inagaki, both of Fuji; Yoshiyuki Mizoguchi, Ohita; Noboru Fujikawa, Tokyo; Naoya Kominami, Fuji, all of Japan

[73] Assignee: Asahi Kasei Kogyo Kabushiki Kaisha, Osaka, Japan

[21] Appl. No.: 637,102

[22] Filed: Dec. 2, 1975

[30] Foreign Application Priority Data

| Dec. 4, 1974 | Japan | 49-138979 |
| Dec. 30, 1974 | Japan | 50-1125 |
| Feb. 24, 1975 | Japan | 50-22620 |
| Feb. 25, 1975 | Japan | 50-23064 |
| Mar. 8, 1975 | Japan | 50-28407 |

[51] Int. Cl.$^2$ ............... B01D 13/00; B01D 21/24; B01D 35/00
[52] U.S. Cl. ............... 210/266; 210/321 A; 210/456; 210/259
[58] Field of Search ............... 210/321, 22, 24, 456, 210/259, 266

[56] References Cited

U.S. PATENT DOCUMENTS

| 3,028,965 | 4/1962 | Isreeli | 210/321 A X |
| 3,228,877 | 1/1966 | Mahon | 210/22 |
| 3,442,002 | 5/1969 | Geary, Jr. et al. | 210/321 X |
| 3,442,389 | 5/1969 | Mendelson | 210/321 A |
| 3,463,728 | 8/1969 | Kolobow et al. | 210/22 |
| 3,944,485 | 3/1976 | Rembaum et al. | 210/24 |

*Primary Examiner*—Frank A. Spear, Jr.
*Assistant Examiner*—D. R. Sadowski
*Attorney, Agent, or Firm*—Armstrong, Nikaido & Marmelstein

[57] ABSTRACT

A dialysis unit and a dialysis apparatus employing the dialysis unit which can perform dialysis at a very high efficiency. The unit comprises a vast plurality of semipermeable hollow fibers substantially equal in length, which fibers are gathered to form a bundle and bonded in liquid-tight connection at both ends portions thereof. This bundle of hollow fibers is loosely encased in a casing having a plurality of openings substantially uniformly distributed all over the casing. The dialysis unit is put in a dialyzate bath having therein a means for making a forced current of the dialyzate. The dialyzate flows into the casing through the openings and acts upon the bundle of hollow fibers from all directions. Accordingly, the dialyzate can flow freely inside and outside the bundle, while maintaining good contact between the dialyzate and the surfaces of the fibers, even in the inner portion of the bundle. Further, as the bundle is protected by the casing, the fibers will hardly break or hardly slip out of the bundle, even though a forced current of the dialyzate is applied thereto. Therefore, the dialysis can be carried out in a short time with high security.

9 Claims, 9 Drawing Figures

DIALYSIS UNIT AND DIALYSIS APPARATUS EMPLOYING THE DIALYSIS UNIT

The invention relates to a dialysis unit employing a bundle of a vast plurality of semi-permeable membranes of hollow fibers (fibrous membrane having continuous or communicating chamber at its center portion, which is to be referred to only as a "hollow fiber" hereinafter), and a dialysis apparatus using said dialysis unit. More particularly, this invention relates to a dialysis unit wherein both terminal end portions of the bundle of hollow fibers are liquid-tightly bonded or fixed and at the both terminals are provided an inlet and an outlet for a liquid flowing through the hollow fibers, and the bundle of hollow fibers is encased in a protective casing having a plurality of openings, and further relates to a dialysis apparatus using said dialysis unit wherein outside liquid, to wit, dialyzate is forcibly made to flow.

Dialysis units employing film- or tube-shaped membrane or hollow fiberous membrane have been used for purification, concentration, or filtration of chemicals in the pharmaceutical industries, for treatment of waste water, and further used as an artificial kidney, an artificial liver or the like for removal of waste materials and intoxicative materials in the medical field. Especially, dialysis unit employing hollow fibers have been remarkably noted, because a vast plurality of hollow fibers can be filled up in a small casing thereby to obtain a large effective dialysis area per volume of the unit.

Especially, when blood is dialyzed through an artificial kidney, an artificial liver, etc. in the medical field, an amount of the blood to be taken out of the body of a patient is limited to about 200 to 300 ml., though there is a difference among individuals. Therefore, when the blood more than the above limit must be taken out, a blood transfusion is required. Accordingly, in order to enhance a dialysis efficiency with a small priming volume of the blood in the dialysis unit, it is necessary to enlarge a dialysis area. For this purpose it has been proposed to use a vast plurality of hollow fibers in a blood dialysis unit.

For example, about 10,000 hollow fibers substantially of equal length are gathered in parallel relationship to one another to form a cylindrical bundle. Both end portions of the bundle are bonded in liquid-tight connection without blocking or crushing a hollow portion of each fiber. The bundle of hollow fibers are put into a cylindrical or prismatical casing having a volume as small as possible and being provided with an inlet and an outlet for dialyzate near both terminal end portions thereof, respectively. The bundle is encased in the casing in such a manner that the hollow portions of the fibers may be in parallel with a central axis of the casing, and the both bonded portions of the fiber bundle are liquid-tightly connected to end walls of the casing, respectively. The both terminal ends of the fiber bundle are connected in liquid-tight connection to tubes for blood to pass, respectively with the communicating distance as short as possible so as to prevent leakage of the blood. The blood is made to pass through the interior of the hollow fibers and a liquid for the dialysis, to wit, dialyzate is made to flow outside the hollow fibers or in the cylindrical or prismatical casing.

However, in the conventional dialysis unit of the type in which blood is brought into contact with the dialyzate in a counter current manner, there is such disadvantage as follows:

When a great number of hollow fibers are filled in the casing, although the dialyzate easily flows along the outer portion of the bundle, namely, along the inner wall of the casing, the dialyzate is difficult to flow through the interior portion of the bundle, leading to the uneven flow of the dialyzate. Accordingly, the dialysis capacity of each hollow fiber, for example, of the hollow fibers at the interior portion of the bundle is not efficiently utilized and the dialysis efficiency is lowered. When such dialysis unit is used as an artificial kidney for cleaning blood of a patient having a kidney trouble, it takes 5 to 8 hours. Further, the patient needs to be subjected to such a long time dialysis treatment two or three times a week, which is a mental and physical burden on the patient.

There have been proposed various attempts to develop a dialysis unit employing hollow fibers of high efficiency and small volume, but any dialysis unit showing good results was not developed yet.

It is therefore an object of the present invention to provide a high-efficiency dialysis unit, making the most of the merits of the hollow fibers such that effective dialysis area is large.

It is another object of the present invention to provide a dialysis apparatus employing the dialysis unit, wherein the dialysis treatment is carried out effectively with high efficiency.

According to one aspect of the present invention, there is provided a liquid dialysis unit comprising:

a protective casing having a plurality of openings for introducing and discharging a dialyzate, said openings being substantially uniformly distributed all over the casing; and a bundle of semi-permeable hollow fibers substantially equal in length, both end portions of the bundle of fibers being gathered and bonded in liquid-tight connection to form fixation blocks, respectively, both terminals of the bundle being opened to form an inlet and an outlet for the liquid, respectively, said bundle being supported within the protective casing at at least two supporting points.

Further, according to another aspect of the present invention, there is provided a liquid dialysis apparatus comprising:

a dialysis unit which comprises a protective casing having a plurality of openings for introducing and discharging a diazylate, said openings being substantially uniformly distributed all over the casing, and a bundle of semi-permeable hollow fibers substantially equal in length, both end portions of the bundle of fibers being gathered and bonded in liquid-tight connection to form fixation blocks, respectively, both terminals of the bundle being opened to form an inlet and an outlet for the liquid, respectively, said bundle being supported within the protective casing at at least two supporting points; and a dialyzate bath having therein a means for making a forced current of the dialyzate; said dialysis unit being fixedly supported in the dialyzate bath.

The inventors of the present invention have made intensive study to provide a dialysis unit having a remarkably high dialysis capacity by making uniform contact between all outer surfaces of the hollow fibers and the dialyzate, and have found the following.

In a dialysis unit comprising a bundle of a vast plurality of hollow fibers the both end portions of which are gathered and bonded by adhesive resins for minimizing a priming volume of the liquid, for example, blood in a dialysis unit, in order to increase the dialysis efficiency, the bundle of the hollow fibers should not be filled tightly in the casing, but be loosely encased in the casing into and out of which the dialyzate can freely flow. Further, an agitating means such as an agitating vane, a pump, or the like may be used to impart to the dialyzate a flow of a direction right-angled to the longitudinal direction of the fiber bundle, thereby to make the dialyzate permeate thoroughly into the interior portion of the bundle. This type is called a forced current type.

According to the present invention, unlike the case where a film- or tube-shaped dialysis membrane is used in a flow of the dialyzate, the dialyzate can be effectively brought into contact with the surface of the hollow fibers from all directions, and the dialyzate current flowing in a direction right-angled with reference to the fiber bundle is disturbed due to a vast plurality of the hollow fibers, while the hollow fibers are given a shake also to disturb the flow of the liquid flowing the interior portions thereof. As a result, unexpected high dialysis capacity can be obtained.

Briefly stated, in the present invention there is provided a dialysis unit wherein a vast plurality of semipermeable hollow fibers are liquid-tightly gathered and bonded in a bundle, and the bundle provided with an inlet and an outlet for the liquid which flows the interior chambers of the hollow fibers is loosely encased in a protective casing having a plurality of openings.

The present invention will be better understood from the following description taken in connection with the accompanying drawings in which.

Figure 2:
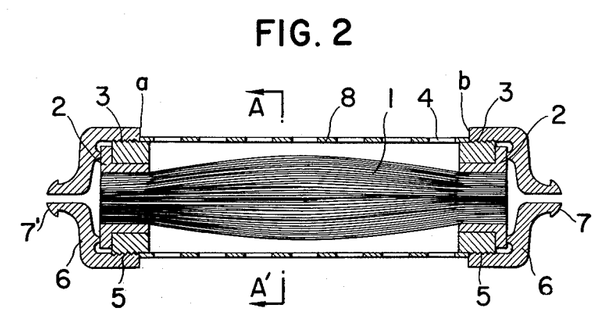
FIG. 2 is a vertical section of one form of a dialysis unit of this invention.
Figure 3:
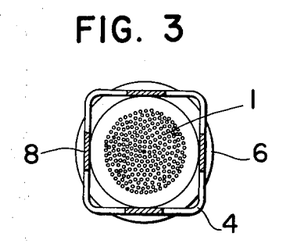
FIG. 3 is a cross sectional end view taken along the line A — A' of FIG. 2.

Referring now to FIGS. 2 and 3, a bundle of hollow fibers 1 has its both end portions bonded and fixed by an adhesive in liquid-tight connection to form a fixation block 2. The bundle of hollow fibers 1 is loosely encased in a protective casing 8 of prismatical shape which has male screw portions 3 at its both end portions, respectively and a plurality of openings 4 all over its wall. A nozzle cap 6 having a female screw portion 5 is screwedly engaged with the male screw portion 3 of the protective casing 8 so that the fixation block 2 may be in close contact with the terminal end portion of the casing and the fiber bundle is liquidtightly connected at its end portions to an introduction tube 7 and a discharge tube 7' for a liquid to be dialyzed, respectively.

When such dialysis unit as explained above is used for cleaning blood, the blood introduced into the dialysis unit through the introduction tube 7 flows the hollow portions of the hollow fiber bundle 1 which is loosely encased in the protective casing 8, said casing constituting the side wall of the dialysis unit itself. Dialyzate capable of freely flowing into and out of the protective casing 8 through the openings 4 formed in the wall of the casing acts upon the blood, from which waste material is sufficiently removed. Then, the dialyzed blood is discharged out of the dialysis unit through the tube 7'.

Figure 4:
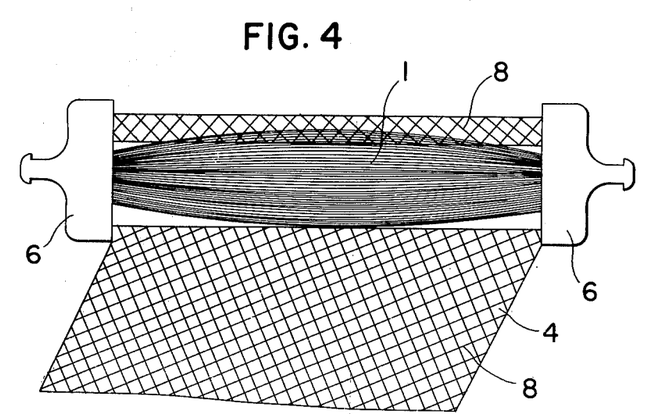
FIG. 4 and FIG. 5 are perspective views, partially exploded, illustrating other forms of protective casings in a dialysis unit of this invention.
Figure 5:
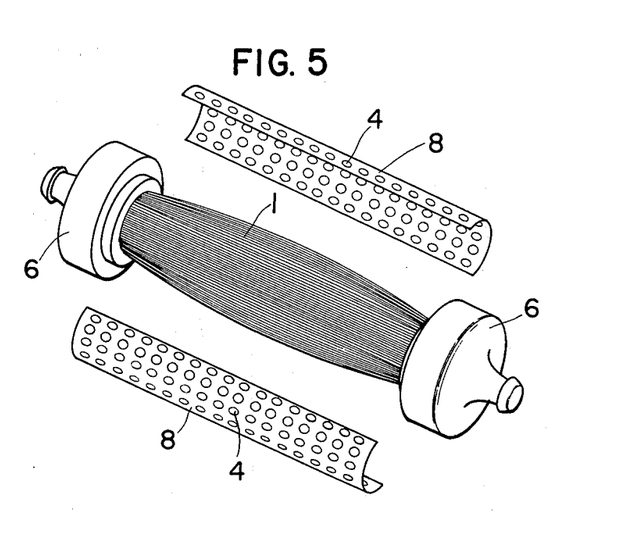

In FIG. 4 is shown a dialysis unit employing a reticulate protective casing and in FIG. 5 is shown a dialysis unit employing a cylindrical protective casing, both partially exploded.

Figure 6:
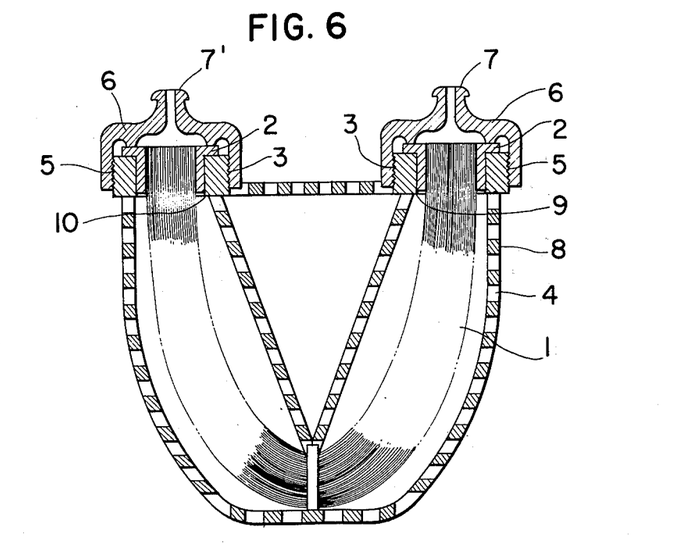
FIG. 6 is a vertical section of another form of dialysis unit of the invention in which a bundle of hollow fibers is fixedly supported in the casing at three points.

Referring to FIG. 6, the bundle of the hollow fibers 1 is supported in the casing 8 at supporting points 9, 10 and 11. Relaxation rates between the points 9 and 10, and between the points 10 and 11 are each kept within a predetermined range of the invention as will be explained hereinafter.

Figure 7:
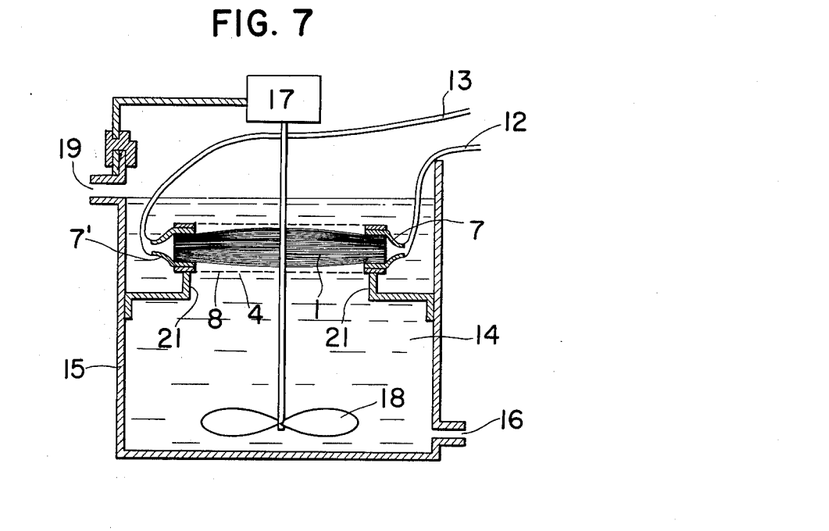
FIG. 7 is a diagrammatical sectional view of a dialysis apparatus of forced current type, employing a dialysis unit of the invention.

Referring to FIG. 7, there is shown one form of a blood dialysis apparatus of forced current type, employing the dialysis unit of the invention. The blood is introduced to the inlet 7 from a blood passage 12 at artery side, passed through the hollow portions of the fibers, and then returned to a human body through the outlet 7' and a blood passage 13 at vein side.

Dialyzate 14 is supplied into a dialyzate tank 15 from an inlet 16 provided at a lower portion thereof. The dialyzate is forcibly stirred by an agitating vane 18 driven by a motor 17 to become a strong stream of the fluid the dialysis unit 8 is fixedly attached to the dialyzate tank 15 by means of a supporting means 21. The stirred dialyzate enters into the dialysis unit 8 through the openings 4 and acts upon the hollow fiber bundle 1. Surplus dialyzate is adapted to overflow out of the dialyzate tank 15 through an outlet 19.

Figure 8:
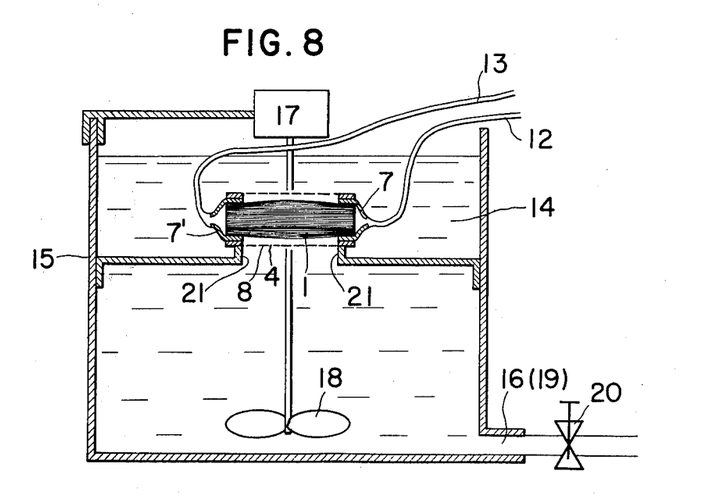
FIG. 8 is a diagrammatical sectional view of another form of a dialysis apparatus of forced current type, employing a dialysis unit of the invention.

FIG. 8 shows in cross section another form of a blood dialysis apparatus of forced current type, employing the dialysis unit of the invention. This embodiment is similar to the embodiment as shown in FIG. 7 except that the dialyzate 14 is stored in the tank 15 through the inlet and outlet 16(19) or directly supplied into the tank 15 from the outside, that a valve 20 is closed during the dialysis treatment, and that the dialyzate 14 is discharged by opening the valve 20 after completion of the blood dialysis.

Figure 9:
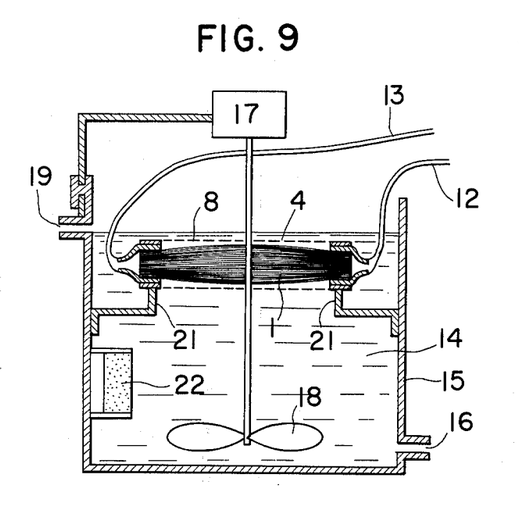
FIG. 9 is a diagrammatical sectional view of one form of a dialysis apparatus of forced current type, employing an absorbing agent in a container and a dialysis unit of the invention.

FIG. 9 shows the same dialysis apparatus as shown in FIG. 7 except that an absorbing agent container 22 is fixedly provided in the apparatus.

The protective casing as is referred to in the present invention need not be limited to a specific one so long as it has such an effect that it can prevent the hollow fibers from being stored up or slipping out of the fixation block due to excessive tension imparted by a forced flow of the dialyzate, and that the dialyzate can freely go into and out of the casing. But some definition is necessary concerning the openings to be formed in the protective casing.

Illustratively stated, when openings each having a cross sectional area (X cm$^2$) in the range defined by the formula $0.001 \leq X < 50$ (cm$^2$) are uniformly distributed all over the wall of the casing with an opening rate (Y%) in the range defined as follows:

when 0.46 ≦ X < 50, 10 ≦ Y < 98 (%); and
when 0.001 ≦ X < 0.46, −30 logX ≦ Y < 98 (%), the dialyzate penetrates into the bundle of hollow fibers very uniformly and a remarkably high dialysis efficiency can be obtained.

Figure 1:
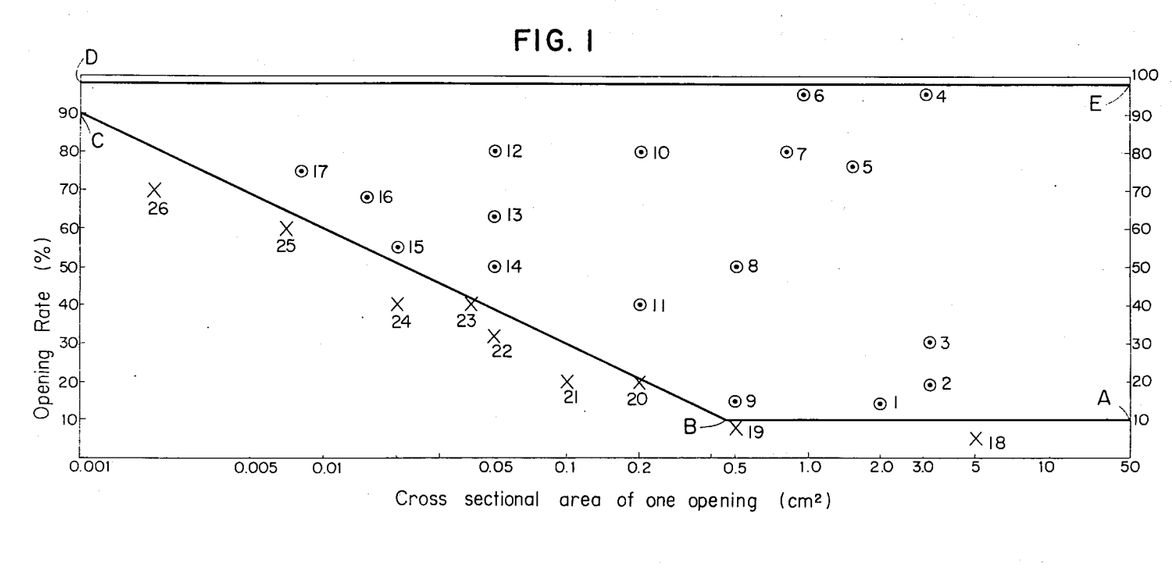
FIG. 1 is a graph showing a range of openings employable, in respect of a cross section area of one opening and an opening rate, in a protective casing of a dialysis unit in accordance with the invention.

FIG. 1 shows a relationship between the size ($X\ cm^2$) and the opening rate ($Y\%$) of the openings in the protective casing wall in accordance with the present invention. In the graph, the abscissa represents the size or the cross sectional area ($X\ cm^2$) of one opening using a logarithmic graduation and the ordinate represents the opening rate ($Y\%$). The range surrounded by the line passing the points A, B, C, D, E and A (except the ranges on a line DE and a line EA) is within the scope of the present invention. The values of X and Y represented by the points A, B, C, D, and E are shown in the following table.

TABLE 1

| Point | Cross sectional area of one opening ($X\ cm^2$) | Opening rate ($Y\%$) |
|---|---|---|
| A | 50 | 10 |
| B | 0.46 | 10 |
| C | 0.001 | 90 |
| D | 0.001 | 98 |
| E | 50 | 98 |

In the present invention, the opening rate is represented by the following formula $$\text{opening rate} = \frac{\text{sum of areas of all openings in the wall of the casing}}{\text{whole area of the wall of the casing (including areas of openings)}} \times 100$$

When a protective casing having an opening rate of less than 10% is used in place of the casing of the present invention, bad influences on the hollow fibers given by a forced current can be prevented but it is difficult to improve the dialysis efficiency. When a cross sectional area of each opening in the protective casing is too large, sufficient protection of the hollow fibers in the forced current of liquid can not be expected and the hollow fibers may sometimes be damaged during transportation or during preparation for the dialysis treatment. Therefore such casing is not applicable as a protective casing. The upper limit of the size of an opening may be as large as 50 cm², though it varies depending upon a shape of the opening. While, the upper limit of the opening rate may be as high as 98% so long as the casing is useful as a protective means, though it varies depending upon shape, material, etc. of the casing. The smaller (than 0.46 cm²) the opening size is, the higher the opening rate must be, which is shown in FIG. 1 by a line BC. When the cross sectional area is smaller than 0.001 cm², the dialyzate can not go into and out of the casing sufficiently and therefore a high dialysis efficiency as desired can not be obtained.

The thickness of the casing wall is not critical, but should be as thin as possible so far as strength permits. A reticulate substance having proper strength may be used. A shape of the opening may be circular, square, rectangular or of any other shapes. It is, however, desirable that openings each have substantially equal size and be uniformly distributed all over the wall of the casing. If the distribution of the openings is uneven, the flow of the dialyzate also becomes uneven thereby not to improve the dialysis efficiency. A preferred example of the materials for the protective casing is a synthetic high polymer substance such as polyethylene, polypropylene, polystyrene, polymethyl methacrylate, ABS resin, polycarbonate, acrylonitrile-styrene copolymer, polyester resin, polyamide resin or the like.

The number of the hollow fibers in a bundle may be above 6,000 and preferably about 8,000 in general, and sometimes more than 12,000. In this case a strong forced current is required to make the dialyzate flow uniformly into the central portion of the fiber bundle. In the present invention, it is preferable that the protective casing may have openings each having a cross sectional area ranging from 0.46 to 50 cm² and the maximum length of 15 cm, and that the openings are substantially uniformly distributed with an opening rate of from 10 to 95%. More preferably, the cross sectional area of one opening may be 0.46 to 10 cm², the maximum length may be 10 cm or less and the opening rate may be 10 to 90%. When the protective casing having a plurality of openings each having a cross sectional area ranging from 0.46 to 10 cm² is employed, more dialyzate can flow through the central portion of the bundle, and even through the dialyzate should flow violently, the damage of the fibers can be prevented.

As hollow fibers of semi-permeable membrane, there may be employed those made of regenerated celluloses, esterified celluloses and synthetic polymeric materials. More specifically, hollow fibers made of cuprammonium cellulose, acetyl cellulose, polyacrylonitrile, polymethyl methacrylate and the like may be used. It is generally preferred that the inner diameter of the hollow fiber be about 100 to about 1,000 μ. The length of the hollow fiber is preferably 150 to 500 mm, and the number of hollow fibers in a bundle is preferably 6,000 to 20,000. To bond and fix the both terminal end portions of the bundle, there may be employed a liquid adhesive of epoxy resins, polyurethane resins, silicone resins, etc.

The bundle of hollow fibers can not demonstrate its capacity sufficiently until it is loosely encased in the protective casing. For example, as shown in FIG. 2, it is desirable to fixedly support the bundle in the casing so that a relaxation rate as defined by the following formula may be 3 to 30%, more preferably 5 to 15%;

$$\text{Relaxation rate} = 100 - \left[\frac{\text{Direct distance between supporting points } a \text{ and } b}{\text{Average length of the hollow fiber between supporting points } a \text{ and } b}\right] \times 100$$

When the relaxation rate is below 3%, the fibers are apt to adhere closely to each other and the dialysis efficiency is lowered. When the relaxation rate is above 30%, the bundle may be twisted to reduce the dialysis capacity.

It is preferred that the diameter of the casing is 1.5 to 6 times, more preferably 2 to 4 times as large as the close package diameter of the bundle. When the diameter of the casing is smaller than the inferior limit the spread of the bundle of fibers is insufficient, the dialyzate is difficult to penetrate the center portion of the bundle and the dialysis efficiency is lowered. On the other hand, when the diameter of the casing is larger than the superior limit, extraordinary tension is applied to the fibers whereby the fibers are made to break and to slip out of the fixation block causing the leakage of the liquid, and the dialysis unit as a whole may be uselessly of a large size. The configuration of the dialysis unit need not be limited to a laterally extended one as shown in FIG. 2, to wit, the bundle of hollow fibers may be used in a bent state. In this case, though the bundle may be fixedly supported at several suporting points, it is necessary that relaxation rate between each two adjacent supporting points be within the range of 3 to 30% to accomplish the dialysis treatment most efficiently.

Now, there will be given an explanation about a dialysis apparatus of the invention. The dialysis unit which has been already illustrated hereinabove is put in a dialyzate bath 15 provided with a means 18 for making a forced current in the dialyzate.

A preferred volume of the dialyzate tank is 5 to 120 l.

As a means for making a forced current in the dialyzate is used a common one such as a pump, an agitating means, etc. Further, as the agitating means is used an agitating vane of oar type, propeller type, turbine type or the like driven by, for example, a motor. When the agitating means rotates at a rate of from 50 to 10,000 rpm, a high dialysis efficiency can be obtained.

The dialyzate tank has two openings, or has one opening and one switch valve for the dialyzate to go in and out.

Referring to FIG. 7, the tank has two openings 16 and 19. Since the dialysis treatment can be carried out while the dialyzate 14 goes in and out, the tank may have a volume of 5 to 50 l., and more preferably of 5 to 10 l.

Referring to FIG. 8, the tank has one opening 16(19) and a switch valve 20. In this apparatus the dialysis treatment is carried out in the closed system, so it is preferred that the tank has a larger volume of 50 to 120 l., and more preferably of 70 to 100 l.

As shown in FIG. 9, a container 22 for containing an absorbing agent therein may be fixed at a predetermined position in the dialyzate tank 15. The dialyzate 14 can freely go into and out of the container. The absorbing agent is used for absorbing waste materials which go on increasing in the dialyzate during the dialysis treatment.

Generally, as an absorbing agent, there may be employed an active carbon for absorbing organic waste materials. It is, of course, possible to use activated alumina, aluminum silicate, etc. together with the active carbon for absorbing inorganic waste materials. As to a container for absorbing agent, there is not any restriction so far as in a part of the container wall there is employed a membrane made of filter paper, filter cloth and the like so that the dialyzate can freely pass through and the absorbing agent can not leak out of the container. Further, the container may be of any shape, for example, a bag-like shape, a cylindrical shape, etc. If the absorbing agent is used without being contained in the container, the dialysis apparatus is soiled and it takes a long time to clean the apparatus after the dialysis treatment. Accordingly, it is preferred to use the container.

The effects attained by this invention will now be illustrated more specifically by reference to the following Examples.

EXAMPLE 1

8,000 of cellulose hollow fibers (the close package diameter of 30 mm$\phi$) prepared according to the cuprammonium process and having an inner diameter of 260 $\mu$, an outer diameter of 300 $\mu$, a thickness of 20 $\mu$ and a length of 350 mm were gathered to form a bundle. The bundle the both end portions of which were bonded in liquid-tight connection was fixed with a relaxation rate of 6% in a prismatical protective casing as shown in FIG. 2 having an outside diameter of 90 mm. In this way, the dialysis unit was prepared.

To form a dialysis apparatus, the dialysis unit was put in a dialyzate tank having a volume of 100 l., which tank is provided with an agitating vane and a motor and has one opening as an inlet and outlet for the dialyzate and a valve as shown in FIG. 8. The unit was put in the bath tank in such a manner that it was wholly soaked in the dialyzate.

Dialysis experiments using the apparatus as a blood dialysis apparatus were conducted, employing various protective casings having various opening rates and various sizes of the opening, respectively as shown in Table 2.

80 l. of commercially available dialyzate [formed by diluting Renasole Solution (trademark of an undiluted dialyzate comprising sodium, potassium, chlorine, magnesium, calcium and glucose, manufactured and sold by Midori Juji) 35 times with distilled water] was fed into the tank and stirred at a rate of 500 rpm by means of an agitating vane composed of two blades each having an outer diameter of 200 mm$\phi$ thereby to form a forced current. As a model blood, an aqueous solution having a urea concentration of 100 mg/dl. was caused to flow at a flow rate of 200 ml/min. The dialysis was conducted at 37° C. The results are shown in Table 2.

As a comparative experiment, 8,000 of cuprammonium cellulose hollow fibers having an inner diameter of 260 $\mu$, an outer diameter of 300 $\mu$ and a length of 350 mm were gathered and arranged in the axial direction to form a bundle, the both end portions of which were bonded by adhesive. The bundle was put in a cylindrical casing provided with an inlet and an outlet for the dialyzate so that the dialyzate might be in contact with the blood in counter-current manner, whereby a heat exchange type dialysis apparatus as conventionally used was prepared. An aqueous urea solution having a urea concentration of 100 mg/dl. was caused to flow as model blood and a commercially available dialyzate was caused to flow at a flow rate of 500 ml/min. The dialysis was conducted at 37° C. The results are also shown in Table 2.

Table 2

| Experiment No. | Cross sectional area of one opening (cm$^2$) | Opening rate (%) | Urea removal rate, 5 minutes after the start of experiment |
| --- | --- | --- | --- |
| No. 1 | 2.0 | 14 | 81 |
| No. 2 | 3.2 | 19 | 83 |
| No. 3 | 3.2 | 30 | 86 |
| No. 4 | 3.0 | 95 | 89 |
| No. 5 | 1.5 | 76 | 87 |
| No. 6 | 0.94 | 95 | 91 |
| No. 7 | 0.80 | 80 | 87 |
| No. 8 | 0.50 | 50 | 87 |
| No. 9 | 0.50 | 15 | 86 |
| No. 10 | 0.20 | 80 | 90 |
| No. 11 | 0.20 | 40 | 86 |
| No. 12 | 0.05 | 80 | 84 |
| No. 13 | 0.05 | 63 | 86 |
| No. 14 | 0.05 | 50 | 83 |
| No. 15 | 0.02 | 55 | 83 |
| No. 16 | 0.015 | 68 | 84 |
| No. 17 | 0.008 | 75 | 81 |
| No. 18 | 5.0 | 5 | 76 |
| No. 19 | 0.50 | 8 | 75 |
| No. 20 | 0.20 | 20 | 78 |
| No. 21 | 0.10 | 20 | 74 |
| No. 22 | 0.05 | 32 | 77 |
| No. 23 | 0.04 | 40 | 78 |
| No. 24 | 0.02 | 40 | 72 |
| No. 25 | 0.007 | 60 | 76 |
| No. 26 | 0.002 | 70 | 70 |

Table 2-continued

| Experiment No. | Cross sectional area of one opening (cm²) | Opening rate (%) | Urea removal rate, 5 minutes after the start of experiment |
|---|---|---|---|
| No. 27 | — | — | 75 |

Note:
Experiments No. 1 – No. 17 are those in accordance with the present invention
Experiments No. 18 – No. 26 are comparative experiments out of the scope of the present invention
Experiment No. 27 concerns with a conventional dialysis apparatus
Cross sectional area and opening rate in each experiment are shown in FIG. 1.

EXAMPLE 2

A dialysis unit was prepared in the following manner 8,000 of cuprammonium cellulose hollow fibers (close package diameter: 30 mmφ) having an inner diameter of 260 μ, an outer diameter of 300 μ, and a length of 350 mm were formed into a bundle the both end portions of which were bonded by adhesive and liquid-tightly connected to a blood inlet and a blood outlet, respectively. The bundle of fibers was covered by a cylindrical protective casing having a diameter of 70 mmφ. The casing had a plurality of openings of the size of 20 × 40 mm and the opening rate was 50%. The relaxation rate of the bundle was 6%.

The dialysis unit was put in the same dialyzate bath having a volume of 100 l. as employed in Example 1, and dialysis of blood was conducted.

As a model blood, an aqueous solution having a urea concentration of 100 mg/dl was caused to flow at a flow rate of 200 ml/min, and 80 l. of a commercially available dialyzate [formed by diluting Renasole Solution (Trademark of an undiluted dialyzate manufactured and sold by Midori Juji) 35 times with distilled water] was kept warm at 37° C. The dialyzate was stirred by means of an agitating vane to form a forced current state.

The urea removal rate as determined 5 minute after the start of the experiment was 92%.

There was not observed a leakage of the model blood which might have been caused by breakage or slipping-out of the hollow fibers.

Same experiments were conducted except that the relaxation rate of the fiber bundle was varied. Average urea removal rate in each experiment was shown in the following Table 3. The results of comparative experiments are also shown in the Table 3.

Table 3

|  | Relaxation rate (%) | Urea removal rate 5 minutes after the start of experiment |
|---|---|---|
| Experiment No. 1 | 3 | 85 |
| Experiment No. 2 | 10 | 90 |
| Experiment No. 3 | 15 | 88 |
| Experiment No. 4 | 20 | 85 |
| Experiment No. 5 | 30 | 83 |
| Comparative Experiment No. 1 | 1 | 78 |
| Comparative Experiment No. 2 | 40 | 76 |
| Comparative Experiment No. 3 | 60 | 62 |

EXAMPLE 3

The same dialysis experiment as in Example 2 was repeated except that a cylindrical protective casing having a diameter of 120 mmφ was employed and a relaxation rate of the fibers was 6%. The average urea removal rate as determined 5 minutes after the start of the experiment was 91%. The leakage of the model blood was not observed.

As a comparative example, the same dialysis experiment was conducted except that a cylindrical protective casing having a diameter of 35 mmφ was employed with a relaxation rate of 6%. 5 minutes after the start of the experiment, the urea removal rate was 78% in average.

Further, as a comparative example, the same dialysis experiment as Example 2 was repeated except that the bundle of hollow fibers was not covered by the protective casing. The average urea removal rate was 92%, but there was caused about 15% leakage of the model blood due to the breakage of the hollow fibers or slip-out of the fibers from the fixation block.

EXAMPLE 4

8,000 of cuprammonium cellulose hollow fibers having an inner diameter of 260 μ, an outer diameter of 300 μ and a length of 350 mm were gathered to form a bundle, the both end portions of which were bonded by adhesive and were connected in liquid-tight connection to an inlet and an outlet for blood, respectively. The bundle was encased in a cylindrical protective casing having a diameter of 70 mmφ and provided with a plurality of openings of a size of 10 × 80 mm with a relaxation rate of 6% to form a dialysis unit. The dialysis unit was put in a dialyzate bath having a volume of 10 l. and provided with an outlet and an inlet for the dialyzate at its upper and lower portions, respectively as shown in FIG. 7 in such a manner that the unit was soaked in the dialyzate. Blood dialysis experiment was conducted as will be explained hereinbelow. Distilled water having a urea concentration of 100 mg/dl was caused to flow as a model blood at a flow rate of 200 ml/min., while outside the dialysis unit a commercially available dialyzate [formed by diluting Renasole Solution (trademark of an undiluted dialyzate manufactured and sold by Midori Juji) 35 times with distilled water] was made to flow at a flow rate of 500 ml/min. at 37° C. The dialyzate was stirred at a rate of 2,000 rpm, by an agitating vane made of two blades each having an outer diameter of 40 mmφ and provided in the dialyzate tank. Dialysis experiment was conducted. The average urea removal rate was 90%.

EXAMPLE 5

6,000 of cuprammonium cellulose hollow fibers having an inner diameter of 260 μ, an outer diameter of 300 μ and a length of 500 mm were gathered to form a bundle, the both end portions of which were bonded by adhesive and connected in liquid-tight connection to an inlet and an outlet for blood. The bundle was fixedly put in a protective casing which had a plurality of openings each having a cross sectional area of about 3.2 cm² and had an opening rate of 30% in such a manner that as shown in FIG. 6, substantially a centeral portion of the bundle was fixed by an annular supporting means 11 and the both ends were supported by supporting means 9 and 10. The bundle of the fibers has a relaxation rate of 10% between the supporting means 9 and 11, and 11 and 10.

Such a dialysis unit was put in a dialyzate bath having a volume of 10 l. and two opening portions for an inlet and an outlet as shown in FIG. 7. With the apparatus, the dialysis was conducted.

Model blood made by dissolving urea in distilled water so as to have a urea concentration of 100 mg/dl was caused to flow at a flow rate of 200 ml/min., while the dialyzate was made to flow at a flow rate of 500 ml/min. at 37° C in the vessel, and was stirred at a rate of 2,000 rpm by an agitating vane made of two blades having a diameter of 40 mm$\phi$. Dialysis experiment was conducted and as a result, a urea removal rate was 87%.

EXAMPLE 6

8,000 of cuprammonium cellulose hollow fibers having an inner diameter of 260 $\mu$, an outer diameter of 300 $\mu$ and a length of 350 mm were gathered into a bundle, the both end portions of which were bonded and fixed by adhesive and connected in liquid-tight connection to an inlet and an outlet for blood, respectively. The bundle was encased in a protective casing with a relaxation rate of 6% to form a dialysis unit. Said casing had a plurality of openings each having a cross sectional area of about 3.2 cm$^2$ and the opening rate was 30%. The dialysis unit was fixedly put in a dialyzate bath as shown in FIG. 9 having a volume of 10 l. and provided with an inlet and an outlet for the dialyzate and a container for containing an absorbing agent. As the absorbing agent, 300 g of granular active carbon of 40 to 60 mesh size were employed, and the container was covered with a wire-netting of 200 mesh size made of stainless steel.

A model blood was prepared by dissolving 3.5 g of creatinine into 35 l. of distilled water (creatinine concentration: 10 mg/dl). The model blood was circulated at a rate of 200 ml/min. While in the dialyzate tank, a commercially available dialyzate formed by dilluting Renasole Solution 35 times with distilled water was caused to flow at a flow rate of 500 ml/min. at 37° C. The dialysis test was conducted while stirring the dialyzate at a rate of 2,000 rpm by means of an agitating vane made of two blades each having an outer diameter of 40 mm$\phi$. Four hours after the start of the experiment a creatinine concentration was 3.9 mg/dl.

As a comparative example, the same bundle of hollow fibers as employed in Example 1 was encased in a cylindrical casing having an inlet and an outlet for the dialyzate in such an arrangement that a counter-current contact was made between the blood and the dialyzate thereby forming a conventional heat exchange type dialysis apparatus. The dialysis was conducted under the same conditions as in Example 6. After five hours, a creatinine concentration in the solution was 4.2 mg/dl.

EXAMPLE 7

The same procedure as in Example 2 was repeated except that in the hollow fibers human blood was passed through and the blood pressure at an outlet of the dialysis unit was adjusted to 100 mmHg.

After 4 hours, a urea concentration and a creatinine concentration in the blood were reduced to 40% and 45%, respectively, and further 1.6 kg of water was removed from the patient by ultrafiltration.

As exemplified above, the forced current type dialysis apparatus employing the dialysis unit of this invention is far superior to a conventional dialysis apparatus in the dialysis efficiency.

Accordingly, when the forced current type dialysis apparatus according to the present invention is used as an artificial kidney or an artificial liver for medical treatment such as the removal of waste materials, intoxicative materials, etc. from a human body, the present apparatus has a higher removal rate of solute in the blood than the conventional apparatus, when compared based on the same priming volume of the blood, and therefore it is possible to terminate the dialysis in a short time. In case the removal rate and the dialysis time are permitted to be the same as those in the conventional apparatus, the priming volume of blood can be highly reduced by reducing the whole surface area of the hollow fiber bundle. Accordingly, when the dialysis apparatus of the present invention is employed for the dialysis of blood, strain on the patient can be greatly lightened. According to the present invention, there can be provided a dialysis unit of high safety in which hollow fibers will hardly break or slip out of the fixation block during the dialysis treatment, and the unit will be hardly damaged during installation and transportation.

Further, according to the present invention, owing to the improved security of the dialysis unit, it can bear high pressure of the liquid and the ultrafiltration rate can be accelerated, and therefore the unit can be utilized for controlling water content of a patient under dialysis treatment.

What is claimed is:
1. A liquid dialysis unit comprising:
a protective casing having a plurality of openings for introducing and discharging a dialyzate, said openings being substantially uniformly distributed all over the casing; and
a bundle of semi-permeable hollow fibers substantially equal in length, both end portions of the bundle of fibers being gathered and bonded in liquid-tight connection to form fixation blocks, respectively, both terminals of the bundle being opened to form an inlet and an outlet for the liquid, respectively, said bundle being supported within the protective casing at at least two supporting points; said semi-permeable hollow fibers being supported and arranged to have a relaxation rate of 3 to 30% at a position between any two adjacent supporting points; and said protective casing having a diameter 1.5 to 6 times as large as the close package diameter of the bundle.

2. A liquid dialysis unit as claimed in claim 1, wherein a cross sectional area of one opening in the protective casing is from 0.001 cm$^2$ to less than 50 cm$^2$.

3. A liquid dialysis unit as claimed in claim 2, wherein the cross sectional area of one opening in the protective casing is from 0.46 cm$^2$ to less than 50 cm$^2$ and an opening rate is from 10 to less than 98%.

4. A liquid dialysis unit as claimed in claim 2, wherein the cross sectional area of one opening in the protective casing is from 0.001 cm$^2$ to less than 0.46 cm$^2$ and the opening rate (Y%) is represented by the following formula $$-30 \log X \leq Y < 98$$

wherein X represents a cross sectional area of one opening.

5. A liquid dialysis apparatus comprising:
a dialysis unit which comprises a protective casing having a plurality of openings for introducing and discharging a dialyzate, said openings being substantially uniformly distributed all over the casing, and a bundle of semipermeable hollow fibers substantially equal in length, both end portions of the bundle of fibers being gathered and bonded in liquid-tight contact to form fixation blocks, respectively, both terminals of the bundle being opened to form an inlet and an outlet for the liquid, respectively, said bundle being supported within the protective casing at at least two supporting points; said semipermeable hollow fibers being supported and arranged to have a relaxation rate of 3 to 30% at a position between any two adjacent supporting points;

a dialyzate bath having therein a means for making a forced current of the dialyzate; said dialysis unit being fixedly supported in the dialyzate bath; said protective casing having a diameter 1.5 to 6 times as large as the close package diameter of the bundle.

6. A liquid dialysis apparatus as claimed in claim 5, wherein the means for making a forced current is a pump.

7. A liquid dialysis apparatus as claimed in claim 5, wherein the means for making a forced current comprises an agitating vane and a driving motor.

8. A liquid dialysis apparatus as claimed in claim 5, wherein the dialyzate bath has at least one opening for the dialyzate to go in and out.

9. A liquid dialysis apparatus as claimed in claim 5, wherein in the dialyzate bath is provided a container for containing an absorbing agent into and out of which the dialyzate freely flows.

* * * * *